United States Patent
Tuli

(10) Patent No.: US 12,383,438 B2
(45) Date of Patent: Aug. 12, 2025

(54) METHOD AND SYSTEM FOR SENSING BOWEL MOVEMENT

(71) Applicant: Raja Singh Tuli, Montreal (CA)

(72) Inventor: Raja Singh Tuli, Montreal (CA)

( * ) Notice: Subject to any disclaimer, the term of this patent is extended or adjusted under 35 U.S.C. 154(b) by 346 days.

(21) Appl. No.: 18/196,865

(22) Filed: May 12, 2023

(65) Prior Publication Data

US 2023/0372162 A1    Nov. 23, 2023

Related U.S. Application Data

(60) Provisional application No. 63/342,703, filed on May 17, 2022.

(51) Int. Cl.
| | | |
|---|---|---|
| *A61F 13/42* | (2006.01) | |
| *G01N 33/00* | (2006.01) | |
| *A61F 13/15* | (2006.01) | |

(52) U.S. Cl.
CPC ......... *A61F 13/42* (2013.01); *G01N 33/0027* (2013.01); *A61F 2013/1513* (2013.01)

(58) Field of Classification Search
CPC .. A61F 13/42; A61F 13/84; A61F 2013/1513; A61F 2013/424; A61F 2013/4506; A61F 2013/49098
See application file for complete search history.

(56) References Cited

U.S. PATENT DOCUMENTS

| | | | | |
|---|---|---|---|---|
| 6,091,336 A | * | 7/2000 | Zand | A61F 13/42 340/573.5 |
| 8,882,731 B2 | * | 11/2014 | Suzuki | A61F 5/451 604/327 |
| 2023/0310202 A1 | * | 10/2023 | Kim | A61F 5/441 604/355 |

\* cited by examiner

*Primary Examiner* — Catharine L Anderson

(57) ABSTRACT

A bowel movement detection and alerting system including a sensing device attached to an absorbent article for alerting a caregiver to the presence of solid waste by analyzing the gasses expelled in the absorbent article during a bowel movement. The system comprises an elongated pipe made of a flexible material and attached to the absorbent article. The pipe is connected to a gas sensor disposed in a pod device that detects a presence of hydrogen sulfide gas to determine an occurrence of a bowel movement or defecation in the absorbent article.

16 Claims, 5 Drawing Sheets

METHOD AND SYSTEM FOR SENSING BOWEL MOVEMENT

BACKGROUND OF THE INVENTION

Field of the Invention

The present disclosure generally relates to a bowel movement detection and alerting system and, more specifically, to a sensing system for collecting sensor signals from a gas sensor attached to an absorbent article of a patient or a user.

Description of Related Art

Disposable absorbent article such as disposable diaper is a product that is capable of receiving and retaining bodily exudates or excretions so as to prevent contamination of the clothing or external environment. As an example, with a disposable diaper, the user is allowed to urinate or defecate without the use of a toilet. In addition to diapers, there are numerous other types of disposable absorbent articles such as e.g. under pads, incontinence pads, fitted briefs, belted shields, liners, all-in-one pads, pull-up incontinence pants, training pants, protective underwear, catamenial napkins, and incontinence guards etc. It is to be understood that the list of disposable absorbent articles identified above is not exhaustive and that these and other absorbent articles can be used with the present disclosure and are within the scope of the present disclosure. It is also to be understood that a reference in this specification to any one such article, such as a "diaper" is to be taken to be a reference to any and all other suitable absorbent articles including incontinence garments, pads and the like.

In order to prevent contamination of the clothing or external environment, disposable absorbent article is provided with an absorbent core capable of receiving and retaining bodily exudates or excretions, and a substantially liquid impervious layer. In general, disposable absorbent products consist of a layered construction, which allows the bodily exudates or excretions to be distributed and transferred to the absorbent core where they are retained in. In everyday use, a disposable absorbent article may be used until the absorbent core is saturated with e.g. bodily exudates or excretions. When the absorbent core is saturated, the disposable absorbent article needs to be removed, disposed of, and replaced with a clean and dry article.

Several methods have been proposed in the art in order to determine saturation of the absorbent core. However, there is a need for efficiently determining the type of bodily exudates saturating the absorbent core. Specifically, there is a need of system for determining whether the core of the absorbent article has been saturated by urine or feces/solid waste. In some methods proposed in the art, a wetness indicator has been added to an absorbent article to detect the presence of urine, and in other methods, a sensor for odor detection has been added to detect the presence of feces or bowel movement. Problems have been encountered in determining the type of excrement present within the absorbent article with these known methods. Therefore, a need exists for an improved system and method of alerting a caregiver about the type of excrement saturating the core of the absorbent article worn by a patient or a user.

SUMMARY OF THE INVENTION

The following summary is provided to introduce a selection of concepts in a simplified form that are further described below in the detailed description. This summary is not intended to identify key features or essential features of the claimed subject matter, nor is it intended to be used to limit the scope of the claimed subject matter.

In various implementations, a bowel movement detection and alerting system can include a sensing device attached to an absorbent article for alerting a caregiver to the presence of urine and solid waste by analyzing the gasses and/or the liquids expelled in the absorbent article. According to an embodiment, the system can comprise a sensor strip containing one or more sensors to detect the presence of solid, liquid and gaseous matter expelled during urination and/or bowel movement of the wearer of the absorbent article. The system can further include a pipe, preferably made of a flexible material such as plastic or rubber, attached to the absorbent article. The gas sensor can be connected to at least one end of the pipe. In a preferred embodiment, the gas sensor is disposed in a pod device and detects a presence of hydrogen sulfide gas to determine an occurrence of a bowel movement or defecation in the absorbent article. In other implementations, a cover sheet preferably made of made of a hydrophobic non-woven material is attached to the pipe, forming a strip. The strip can be adhesively attached to the absorbent article. In some embodiments, the pipe can have perforations along its surface such that gaseous matter is allowed to enter the pipe and liquid matter is not allowed to enter the pipe. In additional embodiments, a hydrophobic material may be applied to one or both ends of the pipe for preventing liquids such as urine from entering the pipe.

In an embodiment, the bowel movement detection and alerting system can include a pod device comprising a coupler for connecting the pipe to the pod device. In other embodiments, the pod device comprises one or more forced air intake devices for periodically drawing air from the pipe and passing the drawn air to the gas sensor. According to one implementation, the gas sensor can be connected to a forced air intake device via a chamber for equalizing the air pressure. In other embodiments of the invention, the bowel movement detection and alerting system can include mechanical and/or cantilever devices for drawing air from the pipe and passing the drawn air to the gas sensor. In some embodiments, air can be drawn from the pipe only when a movement is detected in the body of the patient or user of the absorbent article.

In additional embodiments, the pod device can comprise a humidity sensor in addition to the gas sensor for reducing false positive bowel movement/defecation detections caused due to water vapor generated in a urination event in the absorbent article. In other embodiments, the pod device can be a V-shaped pod device and the pipe may comprise on or more holes for allowing the air inside the pipe to be drawn into the pod device when the pod device is snapped closed on the pipe.

These and other features and advantages will be apparent from a reading of the following detailed description and a review of the appended drawings. It is to be understood that the foregoing summary, the following detailed description and the appended drawings are explanatory only and are not restrictive of various aspects as claimed.

DETAILED DESCRIPTION

Figure 1:
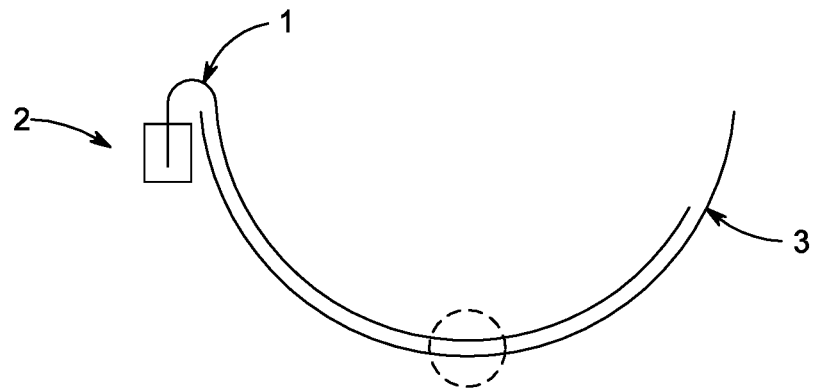
FIG. 1 illustrates an exemplary diaper in accordance with the subject disclosure.

The subject disclosure is directed to a bowel movement detection and alerting system and, more specifically, to a sensing system for collecting sensor signals from a gas sensor attached to an absorbent article of a patient or a user.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

Numerous specific details are set forth in order to provide a thorough understanding of one or more embodiments of the described subject matter. It is to be appreciated, however, that such embodiments can be practiced without these specific details.

Various features of the subject disclosure are now described in more detail with reference to the drawings, wherein like numerals generally refer to like or corresponding elements throughout. The drawings and detailed description are not intended to limit the claimed subject matter to the particular form described. Rather, the intention is to cover all modifications, equivalents and alternatives falling within the spirit and scope of the claimed subject matter.

Now referring to the drawings and particularly to FIG. 1 to FIG. 11, various features of the subject disclosure are now described in more detail with respect to bowel movement detection using a sensing device attached to an absorbent article 3.

FIG. 1 illustrates a plan view of an absorbent article or diaper 3 that has a sensor strip 1 adhesively adhered to the center of the diaper 3. When a sensor strip 1 in matching length and size with the diaper 3 is used, the electrodes in the sensor strip 1 will cover a detection area from the front portion to the rear portion of the diaper 3, corresponding to the region from the groin to the hip of a human body, respectively. The adhesively attached sensor strip preferably contains at least two carbon printed lines to sense the presence of urine in the diaper 3. In the principal embodiment, a certain length of the sensor strip 1 is protruded out of the diaper's front waistband and is intended to be coupled to a wetness event alerting device such as a pod device 2.

Figure 2:
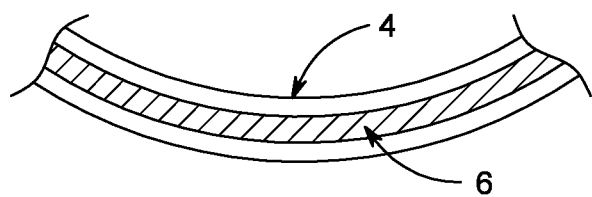
FIG. 2 is a perspective view of an x-axis cross-section of a diaper in accordance with the subject disclosure.
Figure 3:
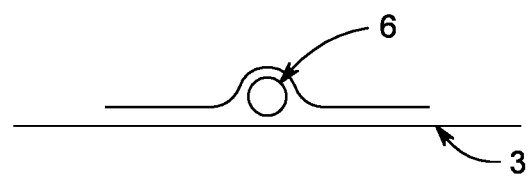
FIG. 3 is a perspective view of the y-axis cross-section of a diaper in accordance with the subject disclosure.

Now referring to FIG. 2 and FIG. 3, various features of the subject disclosure are now described in more detail with respect to bowel movement detection and alerting system using a sensing device inside the absorbent article 3. The bowel movement detection system of the present invention alerts a caregiver to the presence of urine and solid waste by analyzing the gasses and/or the liquids expelled in the diaper 3. In an exemplary embodiment, the sensor strip 1 contains sensors to detect the presence of a gas released during a bowel movement of the wearer of the diaper 3. The sensors may detect a presence of odors associated with urine and solid waste. More specifically, the sensors may detect hydrogen gas, hydrogen sulfide gas ($H_2S$) from certain enzymes and bacteria as well as volatile hydrogen sulfide organic acid gas (RSH), all of which are associated with solid waste. In a preferred embodiment, the sensors will be triggered by the presence of $H_2S$ gas in the diaper 3 above a threshold concentration. However, the sensors may, if desired, be altered so that they will trigger when they detect these gasses individually or when combinations of these gasses are detected. Additionally, in order to prevent false alarms, the pod device 2 could be configured (or programmed) so that it will not indicate that waste has been detected unless the gasses described above are detected for a predetermined period of time.

In another embodiment, the sensor strip 1 contains a thin pipe 6 running along the length of the strip 1 for detecting the presence of one or more gasses released during the bowel movement of the wearer or diaper 3. In certain embodiments, the pipe 6 may have openings at either end to allow gaseous matter to enter and pass through the pipe 6. In a preferred embodiment, the pipe 6 is 1-2 mm in diameter and is made of a flexible material so that pipe does not create discomfort to the wearer of the diaper 3. In some embodiments, the pipe 6 is made of rubber or plastic material. In an alternate embodiment, the pipe 6 may be inserted into the diaper 3. In another alternate embodiment, the pipe 6 may be placed under the sensor strip 1 or be otherwise attached to the strip 1.

FIG. 2 and FIG. 3 are a perspective view of an x-axis and y-axis cross-sections of the diaper 3 in accordance with the subject disclosure. The figures illustrate an embodiment of the bowel movement detection and alerting system of the present invention. As shown in the figures, the pipe 6 and a cover sheet 4 are attached together and form the strip 1. In an embodiment, the cover sheet 4 is made of flexible material that is comfortable for the wearer of the diaper 3. Such flexible material may include plastic material and/or non-woven fabric material. In a preferred embodiment, the cover sheet 4 is made of hydrophobic non-woven fabric material for preventing urine from entering the pipe 6.

The strip 1 also comprises an adhesive on one surface forming a peel and apply mechanism. A caregiver such as a nurse in a hospital may attach the strip 1 to the diaper 3 and further attach one end of the pipe 6 to the pod device 2 through a method disclosed in greater details elsewhere in this patent application. A person skilled in the art may use the strip 1 to sense other bodily fluids including urine by printing carbon lines on the cover sheet 4 or another layer of the diaper 3.

Figure 4:
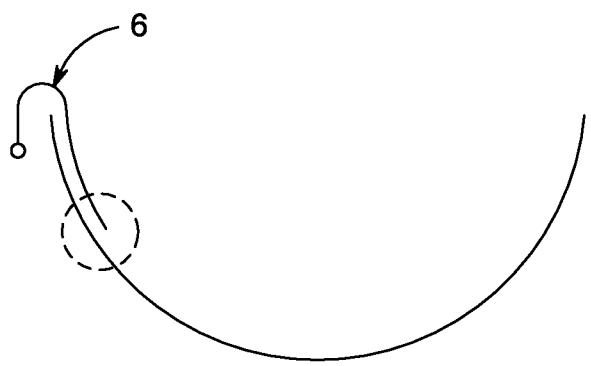
FIG. 4 illustrates both ends of a pipe inside the diaper in accordance with the subject disclosure.
Figure 5:
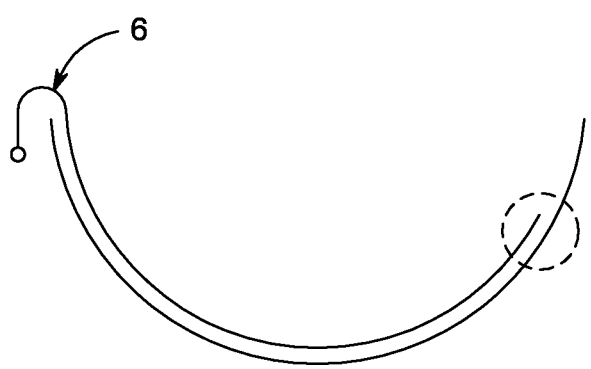
FIGS. 5 and 6 illustrate two different pipe sizes in accordance with different embodiments of the subject disclosure.
Figure 6:
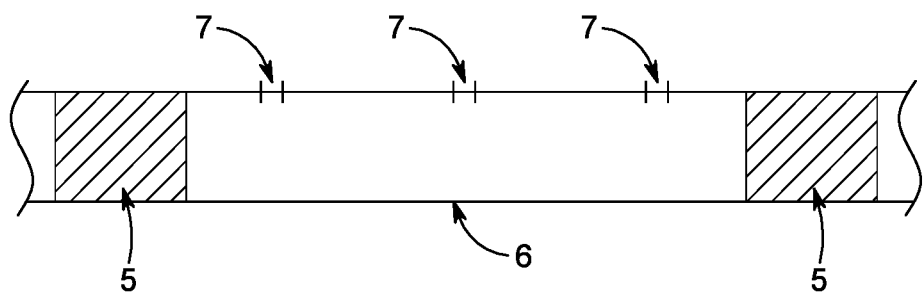

As illustrated in FIGS. 5 and 6, the pipe 6 may be provided in various sizes (lengths) in accordance with different embodiments of the disclosure. In a preferred embodiment shown in FIG. 5, the pipe 6 is very short in length, for example approximately 4 inches, and covers an area from the front waistband of the diaper 3 to the belly region of the wearer of the diaper 3 upon installation. In another preferred embodiment, as shown in FIG. 6, the pipe 6 is long, approximately 25-30 inches, and covers an area from the front waistband of the diaper 3 to the behind the but region close to or beyond the anus region so that gases in that area can get into the pipe 6 of the diaper 3. In both preferred embodiments, the end of the pipe 6 not connected to the pod device 2 is placed in a manner that prevents urine from entering the pipe 6 in case of a urination event in the diaper 3. This allows the pipe 6 to remain unblocked for detecting the presence of one or more gasses released during bowel movement events in the diaper 3. The ends of the pipe 6 are described in greater detail in FIG. 4.

In one embodiment of the invention, the end of the pipe 6 not connected to the pod device 2 may have several preparations to allow more air into the pipe 6. In an alternate embodiment, both ends of the pipe 6 may have special preparations to allow more air into the pipe 6.

As illustrated in FIG. 4, a hydrophobic material 5 may be applied at both ends of the pipe 6 to prevent liquid from entering the pipe 6. In an embodiment, hydrophobic material 5 may be composed of non-polar molecules that repel bodies of water. In case of a urination event in the diaper 3, the hydrophobic material 5 repels the liquid produced during the event and prevents the liquid from entering the pipe 6 and blocking it. In another embodiment, the pipe 6 may have small perforations along its surface that only allow gaseous matter to pass through and enter the pipe 6 and do not allow liquid to enter the pipe 6.

Figure 7:
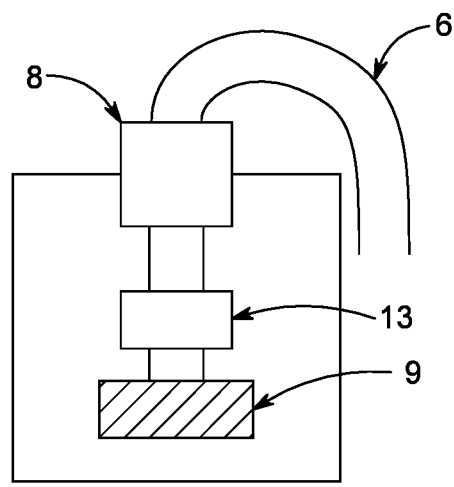
FIG. 7 is a schematic diagram of a pod in accordance with the subject disclosure.

As shown in FIG. 7, the pod 2 may include a coupler 8 to connect the pipe 6 to the pod. The pod 2 may also include a forced air intake device 13, which periodically draws air from the pipe 6 and passes the air to a gas sensor 9 provided in the pod 2 for sensing the one or more gases released during bowel movement events in the diaper 3. In another embodiment, the gas sensor 9 is connected to the forced air intake device 13 through a chamber (not shown in the figure). The chamber equalizes the pressure from the forced air intake device 13 before passing the gasses to the gas sensor 9. In a preferred embodiment, due to the sensitivity of the gas sensor 9 to air pressure, a cavity is provided in the chamber and a low air drawing pressure is applied to the pipe 6. This embodiment allows a low amount of air to enter the chamber without significant changes in the air pressure.

Figure 8:
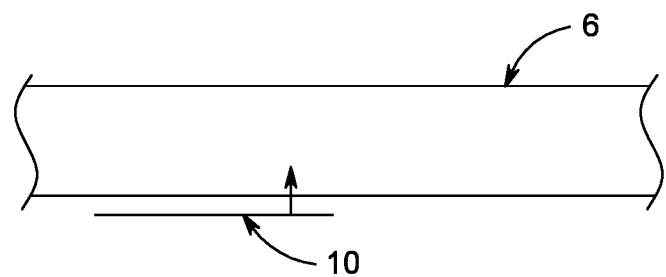
FIGS. 8 and 9 illustrate two different methods of sucking the air inside the pipe in accordance with different embodiments of the subject disclosure.
Figure 9:
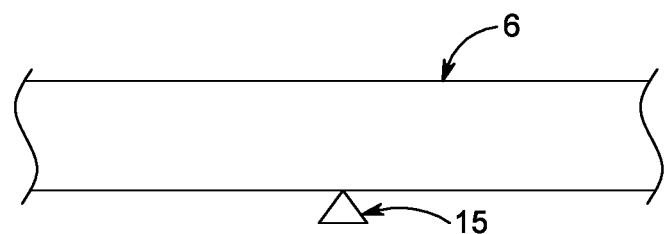

FIGS. 8 and 9 illustrate the process of drawing air from pipe 6 and measuring sensor readings from the gas sensor 9. In the embodiment illustrated in FIG. 8, a piezoelectric cantilever device 10 may be attached to the pipe 6. The piezoelectric device 10 vibrates continuously and pulls the air from the pipe 6. The device 10 may continuously push one side of the pipe 6, causing the pipe 6 to push air in one direction while maintaining constant air pressure.

FIG. 9 describes another embodiment of the invention. In this embodiment, a mechanical intermittent means 15 similar to a system used in hospitals for forcing liquid into bloodstreams may be employed in the pipe 6 to pull air from the pipe and transfer the air to the pod 2. Preferably, a motor may be attached to the pipe 6 for pushing the pipe 6 from outside, thereby bending the pipe 6 and pushing air within pipe 6 into the pod 2.

In a preferred embodiment, the air within pipe 6 is forced into the pod 2 only when movement is detected in the body of the wearer of the diaper 3, indicating a bowel movement in the diaper 3. This embodiment reduces battery consumption of the pod 2.

Referring to FIG. 7, a humidity sensor may be included in the pod 2 to sense humidity and remove false positives from the signals generated by the gas sensor 9. A urination event in the diaper 3 may lead to water vapor being generated in the diaper 3 that may be falsely detected by the gas sensor 9 as bowel movement. In an embodiment of the invention, the humidity sensor may calibrate the signal generated by the gas sensor 9 based on its own measurement of the humidity within the pipe 6. In the event when a urination event in the diaper 3 causes the gas sensor 9 to falsely detect produced vapors as bowel movement, the humidity sensor may reduce the signal level of the signal generated by the gas sensor 9, or may reject the signal generated by the gas sensor 9 as a false positive.

Figure 10:
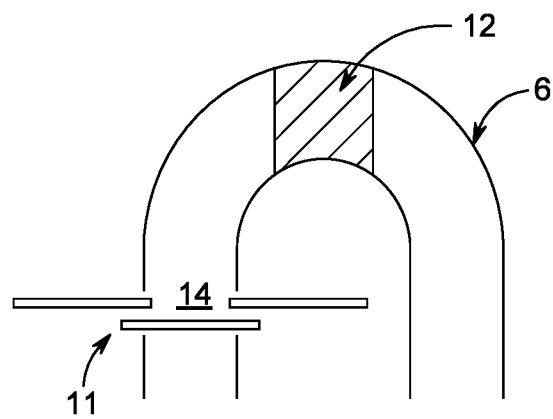
FIG. 10 illustrates a system for connecting a pipe to a pod in accordance with the specific embodiment of the subject disclosure.

FIG. 10 illustrates an exemplary construction of the pod device 2 and the pipe 6 in accordance with the subject disclosure. As illustrated in FIG. 10, the pipe 6 may be connected to the pod device 2 by inserting on end of the pipe 6 into a hole 14 on the pod device 2. Additionally, a pod cover 11 may be included in the pod device 2 for preventing contaminants from entering the pod device 2. In a preferred embodiment, the pod cover 11 may be provided inside or outside the pod device 2 and may automatically cover the pod hole 14 when the pod device 2 is not connected to the pipe 6. In an alternate embodiment, a button may be included on a side of the pod device 2 that may be pressed to open the pod hole 14 and the pipe 6 may be connected to the pod 2 by pushing the pipe 6 through the hole 14. Similarly, the pod 2 may be detached from the pipe 6 by pushing the button and pulling the pipe 6, subsequently closing the pod cover 11 automatically.

Furthermore, the pipe 6 may include liquid impermeable material 12 close to the end of the pipe 6 connected to the pod 2. The liquid impermeable material 12 may allow only gaseous matter to pass through and prevent the contamination of the pod 2 by blocking any non-gaseous matter, as well as micro-organisms such as bacteria and viruses, produced during urination and/or bowel movement events in the diaper 3.

Figure 11:
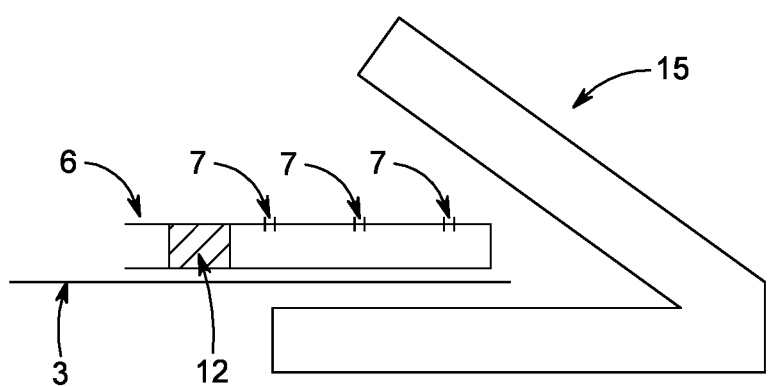
FIG. 11 illustrates a system for connecting a pipe to a pod in accordance with the different embodiment of the subject disclosure.

FIG. 11 illustrates another exemplary construction of a V shaped pod device 15 and pipe 6 in accordance with the subject disclosure. In this embodiment, the end of the pipe 6 to be connected to the pod device 15 is closed and has small holes 7 to allow gaseous matter to pass through the pipe 6 and into the pod 15. The V shaped pod 15 may be attached to this end of the pipe 6, for example by pressing the pod 15 to snap close on the pipe 6, thereby automatically opening the holes in the pod device 15 and allowing the gaseous matter to enter the pod 15 through the holes 7 on the pipe 6.

The detailed description provided above in connection with the appended drawings is intended as a description of examples and is not intended to represent the only forms in which the present examples can be constructed or utilized. It is to be understood that the configurations and/or approaches described herein are exemplary in nature, and that the described embodiments, implementations and/or examples are not to be considered in a limiting sense, because numerous variations are possible.

The specific processes or methods described herein can represent one or more of any number of processing strategies. As such, various operations illustrated and/or described can be performed in the sequence illustrated and/or described, in other sequences, in parallel, or omitted. Likewise, the order of the above-described processes can be changed. Although the subject matter has been described in language specific to structural features and/or methodological acts, it is to be understood that the subject matter defined in the appended claims is not necessarily limited to the specific features or acts described above. Rather, the specific features and acts described above are presented as example forms of implementing the claims.

What is claimed is:

1. A system for detecting a bowel movement in an absorbent article comprising:
   an adhesive strip comprising a pipe attached to the absorbent article;
   a pod device that is removably attached to the absorbent article wherein the pod device is connected to the pipe;
   a mechanical means disposed within the pod device for periodically drawing air from the pipe; and
   at least one gas sensor disposed within the pod device for sensing gases released during the bowel movement.

2. The system according to claim 1 wherein the at least one gas sensor detects a presence of a gas released during a bowel movement including hydrogen sulfide gas in the absorbent article.

3. The system according to claim 1 wherein the pipe is made of flexible material selected from the group consisting of rubber and plastic material.

4. The system according to claim 1 wherein the system further comprises a cover sheet attached to the pipe forming a strip.

5. The system according to claim 4 wherein the said cover sheet is made of hydrophobic non-woven material.

6. The system according to claim 4 wherein the said strip comprises an adhesive on one surface.

7. The system according to claim 1 wherein a hydrophobic material is applied to at least one end of the pipe.

8. The system according to claim 1 wherein the pipe has perforations along its surface such that gaseous matter is allowed to enter the pipe and liquid matter is not allowed to enter the pipe.

9. The system according to claim 1 wherein the at least one pod device comprises a coupler for connecting the pipe to the pod device.

10. The system according to claim 1 wherein the at least one pod device comprises one or more forced air intake devices for periodically drawing air from the pipe and passing the drawn air to the at least one gas sensor.

11. The system according to claim 10 wherein the at least one gas sensor is connected to one or more forced air intake devices through one or more chambers for equalizing air pressure from the one or more forced air intake devices.

12. The system according to claim 1 wherein the system further comprises a piezoelectric cantilever device attached to the pipe for drawing air from the pipe and passing the drawn air to the at least one gas sensor.

13. The system according to claim 1 wherein air inside the pipe is drawn into the at least one gas sensor when a movement is detected in a body of a wearer of the absorbent article.

14. The system according to claim 1 wherein the at least one pod device comprises a humidity sensor for removing false positive measurement signals from the at least one gas sensor.

15. The system according to claim 1 wherein the at least one pod device is a V shaped device connected to the pipe.

16. The system according to claim 15 wherein an end of the pipe connected to the at least one V shaped pod device has one or more holes to allow gaseous matter to pass through the pipe and into the at least one V shaped pod device.

* * * * *